United States Patent [19]
Hagedorn et al.

[11] Patent Number: 5,942,278
[45] Date of Patent: Aug. 24, 1999

[54] PROCESS FOR THE PRODUCTION OF A MATERIAL FOR SEALING AND HEALING WOUNDS

[75] Inventors: Olaf Hagedorn, Warendorf; Ulrich Schiele, München, both of Germany

[73] Assignee: Nycomed Arzneimittel GmbH, München, Germany

[21] Appl. No.: 08/437,232

[22] Filed: May 8, 1995

Related U.S. Application Data

[63] Continuation-in-part of application No. 08/220,877, Mar. 31, 1994, abandoned.

[30] Foreign Application Priority Data

Mar. 31, 1993 [AT] Austria ....................................... 647/93

[51] Int. Cl.[6] ............................. B05D 1/30; B05D 3/12; A61L 15/00
[52] U.S. Cl. .......................... 427/2.31; 118/25; 118/325; 118/612; 222/486; 427/2.12; 427/2.13; 427/394; 427/420; 604/368
[58] Field of Search ..................... 427/2.1, 2.31, 427/394, 420, 2.12, 2.13, 2.14; 222/485, 486; 118/325, 25, 693, 612; 604/304, 368

[56] References Cited

U.S. PATENT DOCUMENTS

| | | | |
|---|---|---|---|
| 1,036,108 | 8/1912 | Harton | 118/25 |
| 1,137,683 | 4/1915 | White . | |
| 1,390,383 | 9/1921 | Powell . | |
| 1,546,411 | 7/1925 | Short . | |
| 2,821,958 | 2/1958 | Litty | 118/25 |
| 3,505,963 | 4/1970 | Westling | 118/25 |
| 3,965,860 | 6/1976 | Cone et al. . | |
| 4,453,939 | 6/1984 | Zimmerman et al. . | |
| 4,683,142 | 7/1987 | Zimmermann et al. | 427/2.31 |
| 5,111,976 | 5/1992 | Ban . | |
| 5,171,367 | 12/1992 | Fitch, Jr. | 118/25 |
| 5,368,563 | 11/1994 | Lonneman et al. | 604/82 |
| 5,464,471 | 11/1995 | Whalen et al. | 106/124 |

FOREIGN PATENT DOCUMENTS

| | | |
|---|---|---|
| 0 472 050 | 2/1992 | European Pat. Off. . |
| 693 222 | 6/1940 | Germany . |
| 201330 | 12/1958 | Germany . |
| 40 00 405 | 7/1991 | Germany . |

OTHER PUBLICATIONS

P.R. Schulz, "Ejection Soldering", IDM Technical Disclosure Bulletin, vol. 5, No. 1 (Jun. 1962), p. 7.

*Primary Examiner*—Diana Dudash
*Attorney, Agent, or Firm*—Wenderoth, Lind & Ponack

[57] ABSTRACT

A process for the production of a material for sealing and healing wounds comprises the even application of a suspension to a collagen carrier. An elongated container, into which the suspension is filled, is provided with a base frame (1) and a set of two perforated plates (2,3) as its bottom. The upper plate (3) is movable and is continuously moved back and forth during the process at a right angle to the transport direction of the collagen carrier, which allows the suspension to drip on the collagen carrier which is transported underneath the container.

16 Claims, 2 Drawing Sheets

PROCESS FOR THE PRODUCTION OF A MATERIAL FOR SEALING AND HEALING WOUNDS

This application is a Continuation-In-Part Benefit of prior application Ser. No. 08/220,877, filed Mar. 31, 1994, now abandoned is hereby claimed under 35 U.S.C. § 120.

BACKGROUND OF THE INVENTION

The invention relates to a process for the production of a material for sealing and healing wounds which comprises the even application of a suspension to a collagen carrier.

A material for sealing and healing wounds which comprises a collagen carrier, coated with a fibrin component, a thrombin component, such as calcium ions, protease inhibitors or heparin antagonists, is known from U.S. Pat. No. 4,453,939.

To prepare this material, the individual components or additives are suspended in an organic solvent, e.g. ethanol, and subsequently applied to a collagen carrier, e.g. by means of spraying.

In doing this, several problems arise, because the suspension to be applied is difficult to handle. For example, the nozzles usually used for these purposes clog immediately. Lignial air nozzles permit the use of a larger diameter, but even in this case, only nozzles with the largest diameter available allow working with a sufficient lack of trouble. However these nozzles show a fatal disadvantage. The indistinct definition of the exiting stream does not apply an even layer of the suspension but creates a trapezoidal coating profile on the collagen carrier. This leads to considerable losses of collagen carrier and valuable suspension at the edges.

A device for applying a liquid film to a fabric web according to the pouring-out principle is known from EP-A 472 050. By means of individual partitions for liquid which are located directly next to one another, this device achieves a forced distribution of the liquid from a feed opening to a number of outflow openings. The liquid is distributed in the form of a family tree, i.e step by step from one opening to two, four, eight, sixteen etc, outflow openings. This device is not suitable for the even distribution of a suspension consisting of fibrinogen and thrombin components, as the several divisions of the liquid stream cause conglutination and clogging of the partitions by the suspension; furthermore, this conglutination and clogging occurs to a greater extent then when nozzles are used.

SUMMARY OF THE INVENTION

The problem solved by the present invention was therefore to prevent the disadvantages of the previously known methods.

The object of the invention is therefore a process for the production of a material for sealing and healing wounds which comprises the even application of a suspension to a collagen carrier, characterized in that an elongated container into which the suspension is filled is provided with a base frame and a set of two perforated plates as its bottom. The upper plate is movable and is continuously moved back and forth during the process at a right angle to the transport direction of the collagen carrier, which allows the suspension to drip on the collagen carrier, which is transported underneath the container.

The container is provided with a rectangular perforated plate (base plate) which is surrounded by the base frame and upon which lateral boundary walls rest. A second perforated plate is mounted directly above the perforated base plate, and this plate can be moved back and forth inside the container as a movable perforated plate.

The suspension to be filled into the container consists of a fibrinogen component, a thrombin component, aprotinin (which acts as protease inhibitor) and other additives such as calcium ions or heparin antagonists in alcohol such as ethanol, n- or i- propanol or n- or i- butanol. This suspension is used for the production of a material for sealing and healing wounds and for other medical uses. For this reason, the device, especially the perforated plates, must be constructed of a material which is abrasion-resistant and chemically inert to the components of the suspension. Suitable materials would be, for example, high grade steel or titanium. The lateral boundary walls can also be constructed of glass or plexiglass, which makes it possible to easily observe the suspension in the container.

BRIEF DESCRIPTION OF THE DRAWINGS

Further features and advantages of the present invention will become clear from the following description thereof, taken in consideration of the drawing figures, in which.

DETAILED DESCRIPTION OF THE PREFERRED EMBODIMENTS

Figure 1:
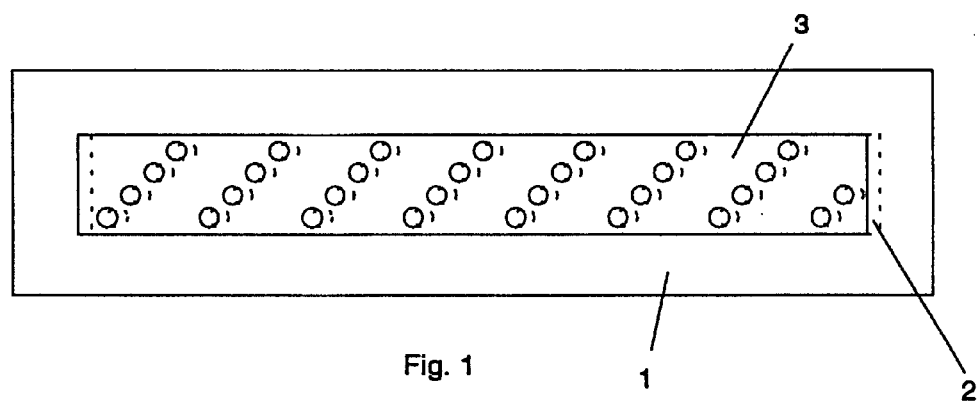
FIG. 1 is a plan view of an elongated container for use with the process according to the present invention.

With a process according to the present invention, an even application of a suspension to a collagen carrier results in the production of a material for sealing and healing wounds. An elongated container into which the suspension is filled is provided with a base frame 1 and a set of two perforated plates 2, 3 forming the bottom of the container. The plate 3 is the upper plate, and is movable. During operation it is continuously moved back and forth at a right angle to the direction of transport of the collagen carrier. This allows the suspension to drip onto the collagen carrier that is transported below the container.

The plate 2 is a base plate, and is a rectangular perforated plate that is surrounded by the base frame 1. A lateral boundary wall of the base frame 1 rests upon the base plate 2. The movable perforated plate 3 is mounted directly above the perforated base plate 2, and it can be moved back and forth inside the container.

The suspension to be filled into the container consists of a fibrinogen component, a thrombin component, aprotinin (which acts as a protease inhibitor) and other additives such as calcium ions or heparin antagonists in alcohol such as ethanol, n- or i- propanol or n- or i- butanol. This suspension is used for the production of material for sealing and healing wounds and for other medical uses. For this reason, the device, and especially the perforated plates, must be constructed of a material that is abrasion resistant and chemically inert to the components of the suspension. Suitable materials include, for example, high grade steel or titanium.

The lateral boundary walls can also be constructed of glass or plexiglass, which makes it possible to easily observe the suspension inside the container.

Both perforated plates are provided with one or more rows of holes, whereby the flow-through holes in the rows are arranged at equal distances. Preferably the plates are provided with several equidistant rows of holes. The diameter of the flow through holes chosen must be large enough to prevent the suspension from clogging them.

The ratio of the flow-through holes' diameter to that of the largest particle in the suspension amounts to approximately 5:1 to 50:1, preferably 7.5:1 to 40:1 and most preferably 10:1 to 30:1. The largest particles in the suspension measure approximately 0.1 mm to 0.2 mm in diameter.

The center of the flow-through holes are preferably located at a distance of approximately 2 to 8 mm, especially preferably at a distance of 3–4.5 mm from the surface of the coating, where the rows of holes are set at a right angle to the transport direction of the carrier. Depending on the number of rows, the distance between the neighboring holes in a row can measure up to 16 mm and more.

In applying the suspension to a collagen carrier, the previously homogenized suspension is pumped into the container at a constant speed, whereby the movable perforated plate lies on top of the perforated base plate in the beginning in such a way as to close the flow-through holes. The sealing should be as efficient as possible and can optionally be assisted by bearing weights being placed on top of the movable perforated plate.

As soon as the suspension in the container has reached the stationary level corresponding to the given pumping speed, the coating apparatus is put into operation. The movable perforated plate is caused to move back and forth over the stationary perforated plate. The two sets of rows become congruent at a certain position (preferably in the middle between the two stationary points at which the movable perforated plate changes direction), and the suspension can drip onto the collagen carrier, which is passed under the coating apparatus.

The level of the suspension in the coating apparatus remains constant during this process provided that additional suspension is pumped in.

The varying deflectional distances of the movable perforated plate allow a wide range for setting the ratio of the intervals of closure and opening. This makes it possible to choose hole diameters of a size where no complications arise and, at the same time, to regulate the drop rate.

In consideration of the arrangement of the holes and the transport speed of the carrier, a distribution pattern of the holes can be achieved where the drops form the corners of equilateral triangles, thus corresponding to layers of spheres packed as tightly as possible.

The perforated plate preferably moves at a right angle to the transport direction of the carrier. The back and forth movement of the movable perforated plate simultaneously ensures that the suspension remains homogenous, so that an even distribution of the components is achieved on the collagen carrier. Mixing can be assisted optionally by means of additional arrangements on the movable perforated plate or by a mixer.

With the aid of the device according to the invention, applying an exactly defined breadth of the suspension is possible without loss of suspension or collagen carrier at the edges.

The profile of the coating achieved after evaporation of the suspension medium is not trapezoidal (as it is when using known spraying techniques) but rectangular.

A comparative test, in which the loss at the edge resulting when using the previously known spraying technique, in which a lignial air nozzle is used, is compared to the loss resulting with the device according to the invention, shows that more than five times more suspension is lost with the lignial air nozzle than with the device according to the invention. A relatively small batch was used in this test. The ratio increases correspondingly as the batch size increases. A loss of suspension during application with the device according to the invention occurs only with the residual volume of suspension remaining in the container after pumping ceases.

EXAMPLE 1

Figure 2:
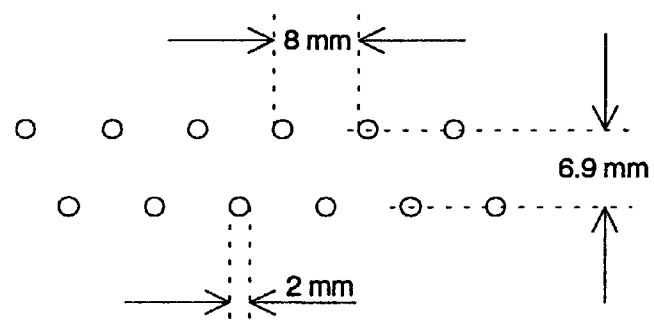
FIG. 2 is a schematic illustration of one example of flow-through holes for the container of FIG. 1.
Figure 3:
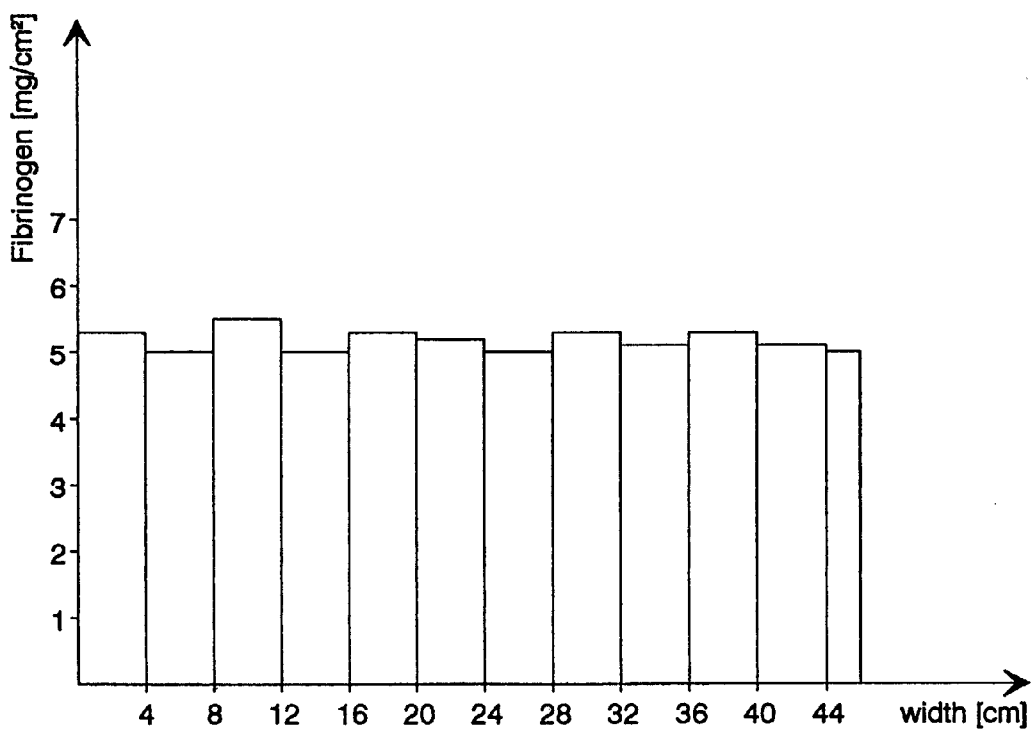
FIG. 3 is a graph illustrating a profile of the amount of coating per square centimeter viewed at a right angle to the direction of transport when a coating is applied according to the process of the present invention.

In a container provided with a perforated base plate and a movable perforated plate with the following dimensions:

Breadth: 450 mm
Depth: 12 mm
Number of rows of holes: 2
Diameter of flow-through holes: 2 mm
Distance between the centers of the two flow through holes located in one row: 8 mm
Distance between the rows of holes: 6.9 mm (The arrangement of the flow-through holes is shown in FIG. 2) in which the perforated plates were closed, a suspension of 55 mg/ml of fibrinogen 20 IU/mi of thrombin and 0.71 Ph. Eur. U/ml of aprotinin in ethanol was pumped at a speed of 450 ml/min until the stationary level of the liquid of 50 mm was reached. At that point, the movable perforated plate was put into motion at 400 cycles/min, whereby the deflection measured 6 mm in both directions. A breadth of 450 mm of the suspension was then dripped onto a collagen sponge measuring 5 mm in height which was being transported underneath the container at a speed of 1 m/min and at a right angle to the movement of the movable perforated plate. After evaporation of the suspension liquid the collagen carrier was coated with approximately 5.5 mg/cm2 of fibrinogen, 2 IU/cm2 of thrombin and 0,071 Ph.Eur.U./cm2 of aprotinin. The loss at the edge was less than 1%. The profile of the coating at a right angle to the direction of transport is shown in FIG. 3.

Comparative Example

Figure 4:
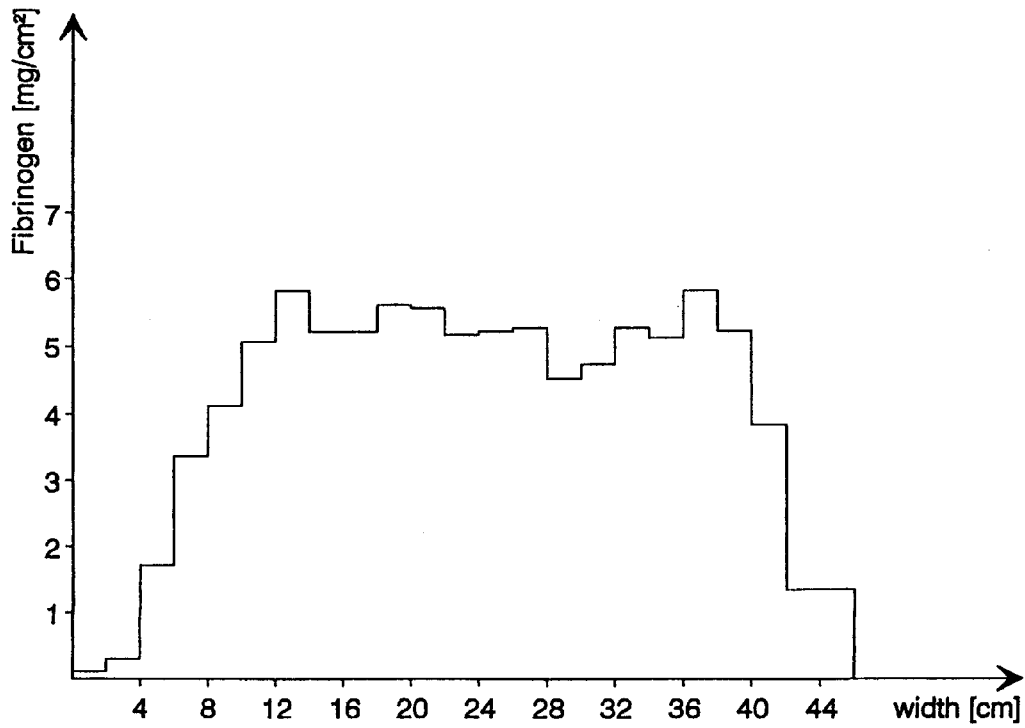
FIG. 4 is a profile similar to FIG. 3, but of the best result achieved in numerous tests with various lignial air nozzles for the application of a suspension to a collagen carrier.

A breadth of 450 mm of a suspension with the same composition was again applied to a collagen carrier which was transported in the same manner as in example 1. FIG. 4 shows the best result achieved in numerous tests with various lignial air nozzles.

In this example, a nozzle combination from Spraying systems Inc., which features a turnaround surface, was used. The best sample was chosen from numerous examples of the same model.

The profile of the coating at a right angle to the direction of transport is shown in FIG. 4, in which the distribution of fibrinogen at a right angle to the transport direction of the carrier is shown. Even under these conditions, the loss of suspension falling from both sides still amounts to approximately 20%.

What we claim is:

1. A process for the production of a material for sealing and healing wounds, comprising:

filling a suspension into an elongated container, the elongated container having a base frame and two perforated plates forming a bottom of the elongated container, the two perforated plates including an upper plate and a lower plate, and the upper plate being movable relative to the lower plate;

transporting a collagen carrier below the elongated container in a transport direction; and continuously moving the upper plate back and forth in a direction that is at a right angle to the transport direction so as to allow the suspension to drip on to the collagen carrier being transported below the elongated container, whereby the suspension is evenly applied to the collagen carrier.

2. The process of claim 1, wherein:

said step of transporting and said step of continuously moving the upper plate back and forth occur simultaneously.

3. The process of claim 1, wherein said step of continuously moving further comprises regulating the flow rate of the suspension by setting a deflection distance of the upper plate.

4. The process of claim 1, wherein the two perforated plates are made from a material selected from the group consisting of steel and titanium.

5. The process of claim 1, wherein the base frame has lateral boundary walls that are made of a transparent material.

6. The process of claim 1, wherein each of the perforated plates comprise at least one row of holes arranged at equal distances with respect to each other.

7. The process of claim 1, wherein the suspension comprises particles therein and the ratio of the diameter of flow through holes in said two perforated plates to the largest of the particles is approximately from 5:1 to 50:1.

8. The process of claim 7, wherein the ratio is approximately 7.5:1 to 40:1.

9. The process of claim 8, wherein the ratio is approximately 10:1 to 30:1.

10. The process of claim 1, wherein said step of filling comprises pumping the suspension into the elongated container at a constant speed with perforations in the two perforated plates being out of alignment such that the elongated container is closed, and wherein said steps of transporting and continuously moving are begun when the suspension in the elongated container has reached a set level.

11. The process of claim 10, wherein the level of suspension is maintained constant during said steps of transporting and continuously moving.

12. The process of claim 1, wherein the suspension comprises a fibrinogen component, a thrombin component and aprotinin, whereby a single layer containing the fibrinogen component and the thrombin component is formed on the collagen carrier during said step of continuously moving.

13. The process of claim 12, wherein the suspension is in alcohol.

14. The process of claim 1, wherein the suspension comprises an organic solvent.

15. The process of claim 1, wherein the two perforated plates comprise respective rows of evenly spaced through holes that are alignable and misalignable with each other in the two perforated plates during said step of continuously moving.

16. The process of claim 1, and further comprising the step of mixing the suspension during said step of continuously moving.

* * * * *